(12) United States Patent
Wuh

(10) Patent No.: US 7,753,955 B2
(45) Date of Patent: Jul. 13, 2010

(54) METHODS AND COMPOSITION FOR SOFT TISSUE FEATURE RECONSTRUCTION

(75) Inventor: Hank C. K. Wuh, Honolulu, HI (US)

(73) Assignee: Cellular Bioengineering, Inc., Honolulu, HI (US)

( * ) Notice: Subject to any disclaimer, the term of this patent is extended or adjusted under 35 U.S.C. 154(b) by 724 days.

(21) Appl. No.: 10/580,559

(22) PCT Filed: Dec. 10, 2004

(86) PCT No.: PCT/US2004/041179

§ 371 (c)(1), (2), (4) Date: Apr. 13, 2007

(87) PCT Pub. No.: WO2005/061019

PCT Pub. Date: Jul. 7, 2005

(65) Prior Publication Data

US 2007/0270948 A1    Nov. 22, 2007

Related U.S. Application Data

(63) Continuation-in-part of application No. PCT/US2004/033194, filed on Oct. 8, 2004, which is a continuation-in-part of application No. PCT/US2004/032934, filed on Oct. 7, 2004.

(60) Provisional application No. 60/528,064, filed on Dec. 10, 2003.

(51) Int. Cl.
*A61F 2/10* (2006.01)
*A61F 2/52* (2006.01)

(52) U.S. Cl. .................. 623/15.11; 623/7

(58) Field of Classification Search ............. 623/11.11, 623/15.11, 7–8; 424/423
See application file for complete search history.

(56) References Cited

U.S. PATENT DOCUMENTS

| 5,041,138 | A | 8/1991 | Vacanti et al. | |
| 5,716,404 | A | 2/1998 | Vacanti et al. | |
| 6,652,872 | B2 * | 11/2003 | Nevo et al. | 424/423 |
| 6,852,330 | B2 * | 2/2005 | Bowman et al. | 424/426 |

FOREIGN PATENT DOCUMENTS

| WO | WO 99/25396 | 5/1999 |
| WO | WO 99/52356 | 10/1999 |

OTHER PUBLICATIONS

Lu et al., "Diamond-Like Carbon as Biological Compatible Material for Cell Culture and Medical Application", Bio-Medical Materials and Engineering, vol. 3, No. 4, pp. 223-228, 1993.

* cited by examiner

*Primary Examiner*—Suzette J Gherbi
(74) *Attorney, Agent, or Firm*—Leydig, Voit & Mayer, Ltd.

(57) ABSTRACT

This present invention describes methods and compositions useful for the reconstruction of various soft tissue features such as lips, areola, and many other features by taking a mold of the skin feature to be replaced, such as the areola, prior to surgical resection, re-creating the size and shape of the soft tissue feature, for example, the nipple and areola, and making a polymer or biopolymer scaffold that is biocompatible, has the ability to allow the epithelization of the skin cells over the polymer, the capability of cell integration into the body of the scaffold, as well as the capability of infiltration of surrounding nerve fibers into the substance of the scaffold, so that the patient may have the benefit of a reconstructed soft tissue feature that not only has the same size and shape and appearance as the native tissue, but also has functional sensation.

3 Claims, No Drawings

METHODS AND COMPOSITION FOR SOFT TISSUE FEATURE RECONSTRUCTION

This patent application is a nationalization of PCT/US04/041179 filed Dec. 10, 2004 and published in English which claims priority to U.S. provisional patent application Ser. No. 60/528,064 filed Dec. 10, 2003, and is a continuation-in-part of PCT/US04/32934 and PCT/US04/33194, and is incorporated by reference herein as if set forth in its entirety.

BACKGROUND OF THE INVENTION

1. Field of Invention

This patent application describes the culturing and implantation of cultured human cells onto synthetic or biosynthetic scaffolds to provide a enervated tissue replacement for use in replacing certain skin and soft tissue features such as finger tips, ears, or more preferably breast to reconstruct the areola or nipple.

2. Description of Prior Art 1 in 8 women in the United States will be diagnosed with cancer of the breast. Therapy for breast cancer remains primarily surgical involving breast mastectomy, quadrantectomy, or other types of resections. Breast cancer surgery can be highly disfiguring despite best efforts on the part of the reconstructive surgeon. The nipple and the areolar regions of the breast are frequently removed during breast resection, and reconstruction of this area has been very difficult. Currently, reconstruction efforts are not able to effectively reproduce neither the appearance, nor the sensation of the nipple and areola.

Tissue culture techniques are being successfully used in developing tissue and organ equivalents. The basis for these techniques involve collagen matrix structures or scaffolds, which are capable of being remodeled into functional tissue and organs by employing the right combination of living cells, nutrients, and culturing conditions. Tissue equivalents have been described extensively in many patents, including U.S. Pat. Nos. 4,485,096; 4,485,097; 4,539,716; 4,546,500; 4,604,346; 4,837,379; and 5,827,641, all of which are incorporated herein by reference. One successful application of the tissue equivalent is the living skin equivalent, which has morphology similar to actual human skin. The living skin equivalent is composed of two layers: the upper portion is made of differentiated and stratified human epidermal keratinocytes that cover a thicker, lower layer of human dermal fibroblasts in a collagen matrix. Bell, et al., "Recipes for Reconstituting Skin," J. of Biochemical Engineering, 113:113-119 (1991).

Cell transplantation has been proposed as an alternative for total organ replacement for a variety of therapeutic needs, including treatment of diseases in the eye, brain, liver, skin, cartilage, and blood vessels. See, for example, J P Vacanti et al., J. Pediat. Surg., Vol. 23, 1988, pp. 3-9; P Aebischer et al., Brain Res. Vol. 488, 1998, pp. 364-368; C B Weinberg and E. Bell, Science, Vol. 231, 1986 pp. 397-400; I V Yannas, Collagen III, M E Nimni, ed., CRC Press, Boca Raton, 1988; G L Bumgardner et al., Hepatology, Vol. 8, 1988, pp. 1158-1161; A M Sun et al., Appl. Bioch. Biotech., Vol. 10, 1984, pp. 87-99; A A Demetriou et al., Proc. Nat. Acad. Sci. USA, Vol. 83, 1986, pp. 7475-7479; W T Green Jr., Clin. Orth. Rel. Res., Vol 124. 1977, pp. 237-250; C A Vacanti et al., J. Plas. Reconstr. Surg., 1991; 88:753-9; P A Lucas et al., J. Biomed. Mat. Res., Vol. 24, 1990, pp. 901-911. The ability to create human cell lines in tissue culture will enhance the prospect of cell transplantation as a therapeutic mode to restore lost tissue function. It is especially vital to be able to create human cultured cell lines from tissues of the neural crest, since tissues or organs derived from that origin couldn't usually repair itself from damage after an individual reaches adulthood.

Conventional tissue culture lab wares useful in growing cells in vitro, are usually coated with a negative charge to enhance the attachment and sometimes proliferation of mammalian cells in culture. However, traditionally it has been most difficult to achieve a satisfactory attachment, maintenance, and propagation of mammalian neuronal cells with the conventional tissue culture surfaces. Adding layers of collagen gel has made improvements or depositing an extracellular matrix secreted by rat EHS tumor cells onto the tissue culture plates and dishes to facilitate neural cell attachment and proliferation. These techniques, however, are hindered by the shortcoming that the material has to be layered on the culture surfaces shortly before the cells are seeded.

The present invention contemplates the use of 3 types of polymers to create a scaffold for cell growth and penetration: biopolymers (polymers formed in a living organism: collagen, gelatin, etc), synthetic polymers (chemically synthesized outside of the body: acrylates, polyvinyl alcohol, etc) and a combination of biosynthetic polymers. The present invention contemplates the use of these polymers as a scaffold to support the attachment, growth, and eventually as a vehicle to supporting the cells during transplantation. This use is vital to the success of cell replacement therapy, particularly in the brain and the back of the eye, where cells derived from the neural crest origin is often damaged during the aging process. There are seven general classes of biopolymers: polynucleotides, polyamides, polysaccharides, polyisoprenes, lignin, polyphosphate and polyhydroxyalkanoates. See for example, U.S. Pat. No. 6,495,152. Biopolymers range from collagen IV to polyorganosiloxane compositions in which the surface is embedded with carbon particles, or is treated with a primary amine and optional peptide, or is co-cured with a primary amine-or carboxyl-containing silane or siloxane, (U.S. Pat. No. 4,822,741), or for example, other modified collagens are known (U.S. Pat. No. 6,676,969) that comprise natural cartilage material which has been subjected to defatting and other treatment, leaving the collagen II material together with glycosaminoglycans, or alternatively fibers of purified collagen II may be mixed with glycosaminoglycans and any other required additives. Such additional additives may, for example, include chondronectin or anchorin II to assist attachment of the chrondocytes to the collagen II fibers and growth factors such as cartilage inducing factor (CIF), insulin-like growth factor (IGF) and transforming growth factor (TGFβ).

SUMMARY OF THE INVENTION

An aspect of the present invention involves the use of a scaffold which involves taking a mold of the skin feature to be replaced, such as the areola, prior to surgical resection, re-creating the size and shape of the soft tissue feature, for example, the nipple and areola, using a scaffold with the following properties: a) biocompatibility; b) the capability of epithelization of the skin tissue over the scaffold; c) the capability of cell integration into the body of the scaffold; d) and the capability of infiltration of nerve fibers into the substance of the scaffold so that the patient may have the benefit of a reconstructed soft tissue feature that not only has the same size and shape and appearance as the native tissue, but also has functional sensation.

An important aspect of the present invention is the use of a custom shaped scaffold comprised of a polymer/biopolymer that promotes nerve infiltration in the soft tissue feature to be replaced or reconstructed. The ability to promote nerve propagation and function is of critical importance and a problem that has not been adequately addressed in prior art.

Another important aspect of the present invention is the creation of a specialized attachment and survival scaffold for the adhesion of many human cell types, including epithelial cells, neuronal cells, and other cells on the microcarriers during the cell transplantation process. The scaffolds used in the present invention can be coated with standard substances known in the art, such as collagen, laminin, and poly-L-lysine, and can also be extra cellular matrix (ECM) proteins secreted by other cells such as tumor cells which are secreted onto the culture surface and then the cells are subsequently removed. We have found that Diamond-like-carbon is a new matrix that can be used for culturing human cells. The DLC coating can be deposited onto microcarriers that are composed of glass, plastics, biopolymer gels, collagen and gelatin, GAGS, synthetic polymers, and metal. The DLC coat can be added on top of other types of coatings such as extracellular matrix (ECM), adhesive molecules, and growth factors.

The mechanical and tribological properties of DLC films (friction coefficient around 0.1 in air, hardness up to about 80 GPa, and elastic modulus approaching 600 GPa) are very close to those of diamond. Moreover, these films are chemically inert in most aggressive environments, and may be deposited with densities approaching that of diamond. However, in contrast to carbon vapor deposition, diamond, DLC films are routinely produced at room temperature, which makes them particularly attractive for applications where the substrate cannot experience elevated temperatures.

It is another aspect of the present invention to teach the deposition of a DLC or other type of coating onto the scaffold surface, which in turn will support the attachment and growth of human and mammalian epithelium, nerve cells as well as other cell types.

In addition to the biopolymers that can be used to construct the scaffold of the present invention, the scaffold can also be comprised of polymers of natural or synthetic in origin. Natural biopolymers comprise collagen and other well known polymeric substances. For synthetic polymers, they can be acrylic and derivatives or copolymers such as polymethyl methacrylate, poly-N-isopropylacrylamide or poly-2-hydroxymethacrylate, polyvinyl alcohols and derivatives and copolymers. The scaffold can either be a thin sheet or in microparticle form. To improve the growth supporting properties of the scaffold, attachment or growth promoting factors can be embedded or incorporated into its composition during synthesis. Furthermore, a three dimensional growth medium suitable for supporting the growth and replication of neural cells comprising of a semi-solid scaffold can also be coated with DLC to enhance its capability to support neuronal growth and maintenance. The scaffold can also be comprised of chitosan or sodium alginate "may polymer" as well.

These and other objects of the invention, as well as many of the attendant advantages thereof, will become more readily apparent when reference is made to the following detailed description of the preferred embodiments.

DETAILED DESCRIPTION AND PREFERRED EMBODIMENTS

In describing embodiments of the invention, specific terminology will be resorted to for the sake of clarity. However, the invention is not intended to be limited to the specific terms so selected, and it is to be understood that each specific term includes all technical equivalents which operate in a similar manner to accomplish a similar purpose.

A primary aspect of the present invention is the use of a polymer/biopolymer scaffold to effect the restoration of shape and look of the soft tissue feature. This restoration includes the molding of the three dimensional shape of the soft tissue feature and the subsequent seeding and growth of human epithelium over the biopolymer/polymer scaffold.

A necessary component of the reconstruction of the soft tissue feature is the subsequent restoration of sensation in the reconstructed area through infiltration and growth of sensory neurons and nerve tracts in the scaffold. The polymer/biopolymer scaffold is permeable so that sensory nerves can grow within the scaffold and enervate it over a period of time. The result is restoration of at least some sensation of feeling in the reconstructed soft tissue part.

It is contemplated that many different soft tissue features may be replicated and reconstructed using the composition and method of the present invention. For example, in addition to the areola, it is contemplated that other parts such as eyelids, fingertips, lips, external genitalia, portions of the ear and nose and many other soft tissue features can be constructed in the manner described within.

As described above, it is contemplated that the bioscaffold used to reconstruct the soft tissue feature of interest is made from a wide variety of materials, for example, such as natural biopolymers comprising collagen and other well known polymeric substances. The scaffold can also be synthesized from synthetic polymers such as acrylic and its derivatives or copolymers such as polymethyl methacrylate, poly-N-isopropylacrylamide or poly-2-hydroxymethacrylate, polyvinyl alcohols and derivatives and copolymers. The polymer scaffold can either be a thin sheet or in microparticle form. Furthermore the scaffold polymers can be coated with standard cellular adhesion proteins like laminin or collagens, as well as the use of DLC and other coatings to enhance attachment of the epithelial cell layers.

The approach of the present invention involves the use of attachment proteins such as fibronectin, laminin, RGDS, collagen type IV, bFGF conjugated with polycarbophil, and EGF conjugated with polycarbophil in or on the scaffold. Polycarbophil is a lightly cross-linked polymer. The cross linking agent is divinyl glycol. Polycarbophil is also a weak poly-acid containing multiple carboxyl radicals which is the source of its negative charges. These acid radicals permit hydrogen bonding with the cell surface. Polycarbophil shares with mucin the ability to adsorb 40 to 60 times its weight in water and is used commonly as an over-the-counter laxative (Equalactin, Konsyl Fiber, Mitrolan, Polycarb) (Park H, et al., J. Control Release 1985; 2:47-57). Polycarbophil is a very large molecule and therefore is not absorbed. It is also non-immunogenic, even in the laboratory it has not been possible to grow antibodies to the polymer.

Recently investigators have reported the use of tethering biologically active molecules to polymer scaffolds for tissue regeneration. See L. Griffith Cima, "Polymer substrates for controlled biological interactions," J. Cell. Biochem., vol. 56, pp. 155-161 (1994); and P. R. Kuhl et al., "Tethered epidermal growth factor as a paradigm for growth factor-induced stimulation from the solid phase," Nature Med., vol. 2, pp. 1022-1027 (1996). By covalently linking epithelial growth factor (EGF) onto a star-poly(ethylene oxide) (PEO) tether and then anchoring the tether onto the surface of a biodegradable scaffold, a 40% increase in rat hepatocyte cell adhesion and migration was shown. See L. Griffith-Cima, "Tissue engineered scaffolds for liver regeneration," Presented at Molecular Engineering of Polymers workshop: Directing Biological Response, American Chemical Society, November 1996.

Moreover, it was also shown that DNA synthesis within the cells was comparable to the levels found when the medium contained free EGF.

Other various embodiments of scaffolding can be used with the epithelial cells for use in reconstruction of tissues. For example, U.S. Pat. No. 5,986,043 discloses photopolymerizable biodegradable hydrogels for use in reducing the formation of cell adhesion after surgery, in applying a drug locally to a tissue surface, and in adhering tissue surfaces in a patient. U.S. Pat. No. 5,906,828 discloses growth effector molecules, including growth factors and extracellular matrix molecules, flexibly linked by branched tethers to a support medium; and the use of the combination to stimulate and support cell and tissue growth. U.S. Pat. No. 5,836,313 discloses a two-layer composite material composed of a thin-layer tissue and a hydrogel that is designed to provide a suitable substrate for corneal epithelial cell growth while maintaining the clarity, flexibility, and diffusivity of hydrogels. Specifically, U.S. Pat. No. 6,689,165 describes the use of a PHEMA/MAA hydrogel. Polymerization of the hydrogel was carried out using a photopolymerization system in a solvent solution that exchanges with water without changes in swelling, useful for corneal epithelial cultures.

Additionally, U.S. Pat. Nos. 5,830,504 and 5,654,267 disclose a composition of an $\alpha_v\beta_3$ integrin ligand and a growth factor receptor ligand combined in a matrix that was said to be useful for promoting wound healing and tissue regeneration. U.S. Pat. Nos. 5,760,176 and 5,120,829 disclose a method to attach a peptide to a solid substrate using its hydrophobic domains. U.S. Pat. No. 5,716,633 discloses a collagen-hydrogel fabricated into an artificial lens, which is capable of promoting epithelial cell growth. U.S. Pat. No. 5,677,276 discloses peptides conjugated to hyaluronate polymers that may be used to promote the healing of wounds and tissue regeneration. U.S. Pat. No. 5,512,474 discloses a cell culture system that comprises a support material with a surface bearing a combination of a positively charged molecule and a cell adhesion factor. U.S. Pat. No. 5,278,063 discloses a method to chemically graft peptides to a surface to enhance cell-surface adhesion to optimize cell culture systems and to improve cell bioadhesion to surfaces made of various materials. U.S. Pat. No. 5,171,264 discloses hydrogels produced by covalently immobilizing polyethylene oxide star molecules onto a support surface. All of the above patents are incorporated by reference into the specification as if set forth in their entireties.

In one embodiment of the present invention there is disclosed a self-sustaining polymer which embeds or has incorporated within the scaffold during it's synthesis, an attachment mixture comprising of one or more of the following: fibronectin, laminin, RGDS, bFGF conjugated with polycarbophil, EGF conjugated with polycarbophil, and heparin sulfate. The scaffold can be molded into any desired shape cultured human epithelial cells will be seeded onto the surface and allowed to proliferate until confluent.

Prior to seeding the epithelial cells onto the scaffold surface, a predetermined mixture of attachment proteins containing fibronectin (ranging from 0.1 µg to 500 µg/ml in PBS), laminin (0.1 µg to 500 µg/ml in PBS), RGDS (0.01 µg to 100 µg/ml in PBS), collagen type IV (ranging from 0.1 µg to 1000 µg in 0.1 M acetic acid) will be added to the denuded surface (Descemet's membrane) and incubated at 4° C. for a period ranging from 5 to 60 minutes. The residual protein mixture will be removed after the incubation period, and the cornea is rinsed three times with PBS and placed endothelial side up on a Teflon mold.

The cultured human epithelial cells will be removed from the tissue culture dish with 0.05% trypsin and 0.02% EDTA in saline solution. The cell suspension will be counted with a Coulter Particle Counter (Z1 model, Beckman-Coulter) and a preparation of about 50,000 to 500,000 cells/ml, preferably about 200,000 cells in 200 µl of culture medium (DME-H16 with 5% fetal calf serum or a serum-free medium containing a mixture of attachment proteins such as fibronectin, laminin, and fibroblast growth factors (at 10 ng to 400 ng/ml) will be added carefully onto the molded bioscaffold. A layer of 1% sodium hyaluronate, such as Healon® (Advanced Medical Optics, Santa Ana, Calif.) at approximately 0.1 to 0.5 ml, will be layered onto the cell suspension as a protectant. The transplanted epithelial cells will then be incubated at 37° C. in a 10% $CO_2$ incubator for a period of 10 minutes up to 24 hours. Alternatively, the coated epithelial cells will be incubated for 20 minutes and the areola will be rinsed three times with PBS at 25° C. and ready for transplantation.

Alternatively, the process of maintaining human epithelial cells in culture, expansion of the areolar epithelial cells, and the preparation of the attachment protein can be used to coat an artificial areola mold bioscaffold made from polymer-gel composition.

Briefly, a poly-gel mold can be molded into a areola shape, and the cell side (epithelial) will be treated with a mixture of attachment proteins and growth factors such as fibronectin (ranging from 0.1 to 500 µg/ml in PBS), laminin (ranging from 0.1 to 500 µg/ml in PBS), RGDS (ranging from 0.01 to 100 µg/ml in PBS), collagen type IV (ranging from 0.1 µg to 1000 µg in 0.1 M acetic acid), FGF (10 to 400 ng/ml in PBS), EGF (10 to 400 ng/ml in PBS), or TGFβ (1 to 100 ng/ml in PBS). After incubation at 4° C. for a period ranging from 10 minutes to 2 hours, the artificial mold will be rinsed three times with PBS, and cultured human areola epithelial cells at a density of about 50,000 to about $10^6$ cells/ml preferably about 150,000 to 250,000 cells/200 ml of culture medium (DMA-H16 with 5% FCS or a mixture of attachment proteins containing fibronectin, laminin, RGDS, and collagen type IV) will be added to the areolar mold. A layer of (10 mg/mL sodium hyaluronate, 0.1 to 0.5 ml) will be applied carefully onto the cell layer as a protectant, and the button will be incubated at 37° C. in a 10% $CO_2$ incubation for a period ranging from 10 minutes to 24 hours. The artificial areola will be rinsed 3 times with PBS.

The methods described in the present invention will allow the coating of a polymer surface with DLC and similar coatings to render it useful as a carrier for cells derived from epithelial origin. The scaffold can be a biodegradable moiety. The scaffold can either be in the form of a thin sheet, in microparticle form, or as a semi-solid block. The scaffold is coated with by using a plasma gun, which will deposit a thin layer of carbon plasma with the thickness of 200 to 400 Å on to the intended culture surface.

Similar to diamond-like carbon (DLC) coating, amorphous carbon nitride (C—N) films can be extremely hard and wear-resistant. They may serve as candidates for the solution to the problem of aseptic loosening of total hip replacements. It has been reported by Du et al., that morphological behavior of osteoblasts on silicon, DLC-coated silicon and amorphous C—N film-deposited silicon in organ culture was investigated by scanning electron microscopy. Cells on the silicon wafers were able to attach, but were unable to follow this attachment with spreading. In contrast, the cells attached, spread and proliferated on the DLC coatings and amorphous C—N films without apparent impairment of cell physiology. The morphological development of cells on the coatings and films was similar to that of cells in the control. The results support the biocompatibility of DLC coating and are encouraging for the potential biomedical applications of amorphous C—N films in the present invention (C. Du et al., Biomaterials. April-May 1998;19(7-9):651-8.

The DLC coating process is as follows:

The plasma equipment consists of a vacuum arc plasma gun manufactured by Lawrence Berkeley National Laboratory, Berkeley, Calif., that is operated in repetitively-pulsed mode so as to minimize high electrical power and thermal load concerns. The fitted with a carbon cathode, the plasma gun forms a dense plume of pure carbon plasma with a directed streaming energy of about 20 eV. The plasma is injected into a 90° magnetic filter (bent solenoid) so as to remove any particulate material from the cathode, and then transported through a large permanent magnet multipore configuration that serves to flatten the radial plasma profile; in this way the carbon plasma deposition is caused to be spatially homogenous over a large deposition area.

To yet further enhance the film uniformity, the substrate(s) to be DLC coated are positioned on a slowly rotating disk, thus removing and azimuthal inhomogeneity. The apparatus described was used to form DLC films of about 2 to 4000 Å thick, preferably about 200-400 Å thick.

To improve the ability of the scaffold in supporting cell growth or attachment, an attachment mixture comprising of one or more of the following will be embedded or incorporated into its composition during synthesis: fibronectin at concentrations ranging from 1 μg to 500 μg/ml of polymer gel, laminin at concentrations ranging from 1 μg to 500 μg/ml of polymer gel, RGDS at concentrations ranging from 0.1 μg to 100 μg/ml of polymer gel, bFGF conjugated with polycarbophil at concentrations ranging from 1 ng to 500 ng/ml of polymer gel, EGF conjugated with polycarbophil in concentrations ranging from 10 ng to 1000 ng/ml of polymer gel, NGF at concentrations of ranging from 1 ng to 1000 ng/ml of the polymer gel and heparin sulfate at concentrations ranging from 1 μg to 500 μg/ml of polymer gel.

In the thin sheet or microparticle forms, the coated scaffold, in another embodiment, is used as a carrier for epithelial or neural cell growth and as a vehicle for cell delivery during a cell transplantation procedure. The semi-solid polymer block form can be used as a neural cell maintenance device in coupling with an integrated circuit chip or a CCD chip to function as a neural stimulation detector. The coated surface can be further improved by coating with an extracellular matrix deposited by cultured bovine corneal endothelial cells and then subsequently overlaid with a DLC coating.

EXAMPLE 1

Coating a biopolymer scaffold in the form of a sheet with DLC.

The biopolymer sheets can be any dimension, preferably about 2 cm×2 cm of the present invention are fixed to a rotating disk which is in turn set up in the DLC coating chamber on top of a slowly rotating motor. The plasma equipment will generate a dense plume of pure carbon plasma via an ejecting gun with a directed streaming energy of about 20 eV. The plasma is injected into a 90° magnetic filter to remove any particulate material to form a high quality, hydrogen free diamond-like carbon. When transported through a large permanent magnet multipore configuration that serves to flatten the radial plasma profile, a carbon plasma deposition will be spatially homogenous over a large deposition area. As the carbon plasma plume approaches the slowly rotating disk holding the polymer sheet, a uniform film of DLC will coat the surface of the sheet. The sheet can be used for growing many kinds of cells, such as epithelial cells, or as a vehicle for cell transplantation after sterilizing with UV radiation or 70% alcohol rinse.

EXAMPLE 2

Coating of biopolymer scaffolds in the form of microparticles with DLC.

The biopolymer microparticles will be placed into a specialized rotating chamber and a plume of carbon plasma is generated as previously described in Example 1. The plasma gun will introduce the spray of DLC into the chamber while it is rotated slowly in a vertical axis. The microcarrier beads will be induced to suspend by an air current in the coating chamber, the beads are allowed to rise and descend in the alternating air current many times while the plasma gun is in operation to insure uniform coating of all sides. This process will be sustained over a period of about 2-3 hours to insure uniform and complete covering of all particle surfaces. A thin layer of DLC at the uniform thickness of about 200-400 Å will be deposited on the entire spherical surface. The product can then be sterilized by UV irradiation or alcohol rinse, packaged and sealed, and stored on the shelf until used.

EXAMPLE 3

Biopolymer scaffolds with attachment or growth promoting factors embedded or incorporated into its composition during synthesis and subsequently coated with DLC.

Scaffolds of the present invention can be embedded with, or incorporated into its composition during synthesis, attachment or growth promoting factors comprising of one or more of the following: fibronectin at concentrations ranging from 1 μg to 500 μg/ml of polymer gel, laminin at concentrations ranging from 1 μg to 500 μg/ml of polymer gel, RGDS at concentrations ranging from 0.1 μg to 100 μg/ml of polymer gel, bFGF conjugated with polycarbophil at concentrations ranging from 1 ng to 500 ng/ml of polymer gel, EGF conjugated with polycarbophil in concentrations ranging from 10 ng to 1000 ng/ml of polymer gel, NGF at concentrations of ranging from 1 ng to 1000 ng/ml of the polymer gel and heparin sulfate at concentrations ranging from 1 μg to 500 μg/ml of polymer gel. The scaffold is then made into thin sheet or a semi-solid bloc, and DLC deposition can be achieved as previously described in Example 1. Or the polymer can be made into micro-particles or spheres, and DLC deposition can be achieved as previously described in Example 2.

EXAMPLE 4

Coating of scaffold with extracellular matrix deposited by cultured bovine corneal endothelial cells and subsequent coating of the sheet or microparticles with DLC.

The biopolymer or polymer sheet, and block of microparticles can first be coated with an extracellular matrix (ECM) prior to the DLC deposition on the culture surface. To achieve this, bovine corneal endothelial cells (BCE) are seeded at low density (about 2000 to 150,000 cells/ml, preferably about 20,000 cells/ml) onto the surface of the sheet or block, or allowed to attach to the surface of the microparticles. The BCE cells are maintained in culture medium containing DME-H16 supplemented with 10% calf serum, 5% fetal calf serum, 2% Dextran (40,000 MV) and 50 ng/ml of bFGF. The cells are incubated at 37° C. in 10% $CO_2$ for 7 days, during which time bFGF at a concentration of 50 ng/ml is added every other day. The BCE cells are removed by treating the polymer sheet, block, or microparticles with 20 mM ammonium hydroxide for 5 minutes. Then the biopolymer with the extracellular matrix coat is washed ten times with sufficient volume of PBS. After drying, the ECM coated polymer sheet or block is subjected to DLC deposition as previously described in Example 1, whereas the ECM-coated microparticles is subjected to DLC deposition as described in Example 2. After the sequential coating with ECM and DLC, the polymer sheet, block, or microparticle will be sterilized by V irradiation or alcohol rinse, and used for neural cell growth or as a vehicle for cell transplantation.

EXAMPLE 5

DLC deposition on the culture surface of tissue culture lab ware.

In the event of a flat culture surface such as a dish, filter insert, chamber slide, sheets, and blocks, the wares can be presented to the plasma gun with the culture surface upwards in the vacuum chamber, and the coating process can proceed as previously described. In the case of the microcarrier beads, they need to be induced to flow in the chamber to insure uniform coating on all sides. For enclosed surfaces like flasks and tubes, a special modified plasma gun will be inserted into the vessel and coat the desired surface. A thin layer of DLC at the uniform thickness of about 20 to about 4000 Å, preferably about 200-400 Å will be deposited onto the culture surface. The products can then be sterilized by UV irradiation or alcohol rinsing, packaged, sealed, and stored on the shelf until use.

EXAMPLE 6

Sequentially coating the culture surface with ECM secreted by cultured bovine corneal endothelial cells and then DLC deposition.

In this embodiment, sparse cultures (about 1000 to about 50,000 cells/ml, preferably 2000-5000 cells/ml) of bovine corneal endothelial cells are seeded onto the culture surface of the intended lab ware, which includes dishes, flasks, tubes, filter inserts, chamber slides, microcarrier beads, roller bottles, cell harvesters, sheets, and blocks. The cells are maintained in a medium containing DME-H16 supplemented with 10% calf serum, 5% fetal calf serum, 2% Dextran (40,000 MV), and bFGF at 50 ng/ml. The bovine corneal endothelial cells are grown for 7-10 days until confluence with bFGF added every other day at 50 ng/ml. Then the culture medium is removed and the cells are treated with sufficient 20 mM ammonium hydroxide in distilled water for 3 to 30 minutes. The surface is then washed with a sufficient amount of PBS 10 times to remove and residual ammonium hydroxide and dried in a sterile laminar flow hood. The coating of DLC can then be performed as previously described on top of the extracellular matrix. The product is then sterilized under UW radiation or alcohol rinse, and will be packaged, sealed, and stored on the shelf until use.

EXAMPLE 7

Sequential coating of the culture surface by attachment or growth promoting reagents followed by DLC deposit.

In this alternate embodiment, one or more of the attachment or growth promoting reagents comprised of fibronectin at concentrations ranging from 1 μg to 500 μg/ml, laminin at concentrations ranging from 1 μg to 500 μg/ml, RGDS at concentrations ranging from 0.1 μg to 100 μg/ml, bFGF conjugated with polycarbophil at concentrations ranging from 1 ng to 400 ng/ml, EGF conjugated with polycarbophil in concentrations ranging from 10 ng to 1000 ng/ml. The attachment or growth promoting reagents will be added to the culture surface, and then will be incubated at 4° C. for 20 minutes to 2 hours. The surface is then rinsed with PBS three times and dried in a sterile laminar flow hood. Then the product will be deposited with a DLC layer on top of the attachment or growth promoting reagent coat on the culture surface. The lab ware will then be sterilized by UV irradiation or alcohol rinse, packaged, sealed, and stored until use.

EXAMPLE 8

Attachment and culture of RPE and other neuronal cells onto the coated microcarriers.

Retinal Pigmented Epithelial (RPE) cells are grown in a 60 mm tissue culture dish previously coated with extracellular matrix (ECM) derived from bovine corneal endothelial cells. The RPE cells are fed every other day with culture media containing 15% fetal calf serum (FCS) and bFGF at a concentration of 100 ng/ml. At confluency, the media is changed and 5 ml of fresh medium is added. Then $5-10 \times 10^6$ microcarrier beads, which are previously coated with DLC or other combinations, are added to the dish. The dish is swirled 8-10 times in a figure-8 motion to endure most of the beads are well distributed, and is then incubated at 37° C. in 10% $CO_2$ and the microcarriers are allowed to settle at the bottom in direct contact with the RPE cells. A solution of bFGF at concentrations of 100 ng/ml is added every other day to the culture, and 2.5 ml of media will be aspirated very carefully from the top with great care to disturb the microcarriers as little as possible. The layer of RPE cells from the dish will gradually attach to the microcarrier beads and start to proliferate around it until it forms a layer covering the total surface area of the microcarrier beads in 7 to 10 days after the beads are introduced to the culture dish. The microcarriers are then gently detached from the cell layer and further cultured in a roller bottle for 3 days, after which, they are ready to be used for injection into the brain stem for the cell transplantation procedure.

EXAMPLE 9

Nerve regeneration within a biosynthetic polymer or hydrogel scaffold for nipple reconstruction.

N-polyisopropylacrylamide/gelatin interpenetrating networks containing 0.5 to 5% gelatin are synthesized by the following procedure. A concentrated N-isopropylacrylamide (NIPAAM) solution is prepared by dissolving 3.98 g NIPAAM, 0.068 g N,N'-methylenebis(acrylamide), and 0.122 mL of N,N,N',N'-Tetramethylthylene diamine in sufficient deionized water to achieve a total volume of 25 mL. An aqueous solution of 5.16% gelatin (w/w) in deionized water was prepared by dissolving the appropriate amount of gelatin in deionized water. A potassium persulfate (KPS) solution is prepared by dissolving 0.12 g potassium persulfate in 5 mL deionized water. The solutions are stored at about 4 to 6° C. until used.

Polymerization of NIPAAM: The gelation solution is heated to about 55° C. while stirring until the gelatin melted completely. After the gelatin solution is cooled to about 30 to about 35° C., 1.53 mL of the gelatin solution is mixed with 1.47 mL deionized water, and then 3.0 mL NIPAAM solution is added. The mixture is stirred for several minutes, and then 0.12 mL KPS is added to the mixture. The mixture is then immediately injected into a mold having the shape of human nipple. The mold is placed in a sealed vessel. Oxygen is removed repeatedly by degassing the mixture using nitrogen at least three times. The mixture is allowed to polymerize for at least two hours at room temperature.

Cross-linking of gelatin: After complete polymerization, the gel is removed from the mold and immersed into an aqueous solution of 0.5% gluctaric dialdehyde to cause the gelatin chains inside the PNIPAAM gel to become cross-linked, thereby forming an interpenetrating network. The resultant gel nipple scaffold is washed with deionized water over the course of several days (by changing the water each day) to remove remaining small molecules and unreacted NIPAAM monomers. The clean gel nipple scaffold is stored at 4 to 6° C.

Implantation and clinical evaluation. Following the standard breast reconstruction procedures, the biosynthetic PNIPAAM/gelatin nipple scaffold is sutured onto the reconstructed breast and is examined daily for 7 days after the operation and then weekly. Nipple touch sensitivity was measured by using Cochet-Bonnet esthesiometer (Handaya, Tokyo) at five points on the nipple. In brief, a fine filament was extended from this tool to contact the nipple and a feeling response of the subject is recorded. Initially, very soft contact is made by using a long filament extension, which is then shortened progressively (becoming stiffer and the touch firmer) until the subject clearly responds. The extension is recorded as the touch-sensitivity threshold.

EXAMPLE 10

Neuronal Regeneration within Reconstructed Areola

It has been shown that neurotrophic factors stimulate peripheral nerve regeneration. The soluble factors applicable to the biosynthetic scaffold nipples include but not limited to acidic fibroblast growth factor (aFGF), basic fibroblast growth factor (bFGF), nerve growth factor (NGF), glial growth factor (GGF), brain-derived neurotrophic factor (BDNF), ciliary neurotrophic factor (CNTF), platelet-derived growth factor (PDGF), and insulin-like growth factor 1 (IGF-1).

PNIPAAM/gelatin gel nipple scaffolds are prepared as described in Example 1. Growth factors discussed are then added to the gel when it is free from small molecules and unreacted NIPAAM monomers. The growth factor enriched gel nipple is then stored at 4 to 6° C. until needed for implantation.

EXAMPLE 11

Modified Biopolymer Scaffold Embodiments

Following the preparation method described in Example 1, poly(n-isopropylacrylamide) can be modified by copolymerization with a monomer selected from the group consisting of acrylate, acrylic acid, methacrylate, methacrylic acid, acrylamide, methacrylamide, vinyl acetate, styrene, and derivatives thereof. It should be understood that a variety of biodegradable polymers and polymers of biological origin can be substituted for the acrylamide polymers of the present invention.

EXAMPLE 12

Gelatin Based Scaffolds

In an alternate embodiment, following the preparation method described in Example 10, gelatin is substituted by collagen or a combination of gelatin and collagen. The method is then followed as in Example 10.

Having described the invention, many modifications thereto will become apparent to those skilled in the art to which it pertains without deviation from the spirit of the invention as defined by the scope of the appended claims. The disclosures of U.S. patents, patent applications, and all other references cited above are all hereby incorporated by reference into this specification as if fully set forth in its entirety.

The invention claimed is:

1. A biocompatible substrate for the cosmetic reconstruction of a mammalian soft tissue feature or region comprising:
   a) a scaffold comprising a polymer, biopolymer or combination thereof in a thin sheet, microparticle or semi-solid block form;
   b) embedding or incorporating into the scaffold; during its synthesis attachment or growth promoting reagents consisting essentially of one or more of the following: laminin, fibronectin, RGDS, bFGF conjugated with polycarbophyll, EGF conjugated with polycarbophyll, and heparin sulfate; and
   c) wherein the scaffold is molded into the shape of a mammalian skin epithelial feature or region.

2. The biocompatible substrate of claim 1, wherein the soft tissue features to be reconstructed can be any soft tissue feature such as a human ear, areola, nose, lip, genitalia, fingertip, and nail bed.

3. The biocompatible substrate of claim 1, wherein the scaffold is selected from the group comprising:
   a) natural polymers including but not limited to collagen, gelatin, hyaluronate, fibrin and alginate;
   b) synthetic polymers including but not limited to polyacrylic acid and derivatives, polyethylene oxide and copolymers, polyvinyl alcohol, polyphosphazene, polypeptides; PNIPAAM/gelatin; NIPAAM; and
   c) further compositions comprising mixtures of natural polymers in a) and synthetic polymers in b).

* * * * *